United States Patent
Zimmerman

(10) Patent No.: US 7,528,599 B2
(45) Date of Patent: May 5, 2009

(54) EDDY CURRENT PROBE

(75) Inventor: Jason Scott Zimmerman, Sumner, WA (US)

(73) Assignee: Matrix Enterprises, LLC, Sumner, WA (US)

( * ) Notice: Subject to any disclaimer, the term of this patent is extended or adjusted under 35 U.S.C. 154(b) by 0 days.

(21) Appl. No.: 10/851,699

(22) Filed: May 21, 2004

(65) Prior Publication Data

US 2008/0278157 A1    Nov. 13, 2008

(51) Int. Cl.
*G01N 27/90* (2006.01)
*G01R 33/12* (2006.01)

(52) U.S. Cl. ........................ 324/242; 324/220

(58) Field of Classification Search ................. 324/220, 324/219, 222, 228, 232, 239, 240, 241, 242, 324/326, 329, 253–255
See application file for complete search history.

(56) References Cited

U.S. PATENT DOCUMENTS

| | | | | |
|---|---|---|---|---|
| 2,904,745 | A * | 9/1959 | Bugg | 324/239 |
| 3,395,339 | A * | 7/1968 | Brown, Jr. | 324/238 |
| 4,524,342 | A * | 6/1985 | Mas | 336/182 |
| 5,068,608 | A | 11/1991 | Clark, Jr. | |
| 5,134,367 | A | 7/1992 | Griffith | |
| 5,199,178 | A * | 4/1993 | Tong et al. | 33/361 |
| 5,237,270 | A | 8/1993 | Cecco | |
| 5,623,204 | A | 4/1997 | Wilkerson | |
| 6,281,678 | B1 | 8/2001 | Auville | |

* cited by examiner

*Primary Examiner*—Kenneth J Whittington
(74) *Attorney, Agent, or Firm*—Christensen O'Connor Johnson Kindness PLLC

(57) ABSTRACT

An eddy current probe moves along a longitudinal axis and includes a support structure defining a surface, the surface including a set of panels. Conductor coils are distributed across said surface, each panel includes at least one coil section, each coil section lies transverse to the longitudinal axis.

10 Claims, 4 Drawing Sheets

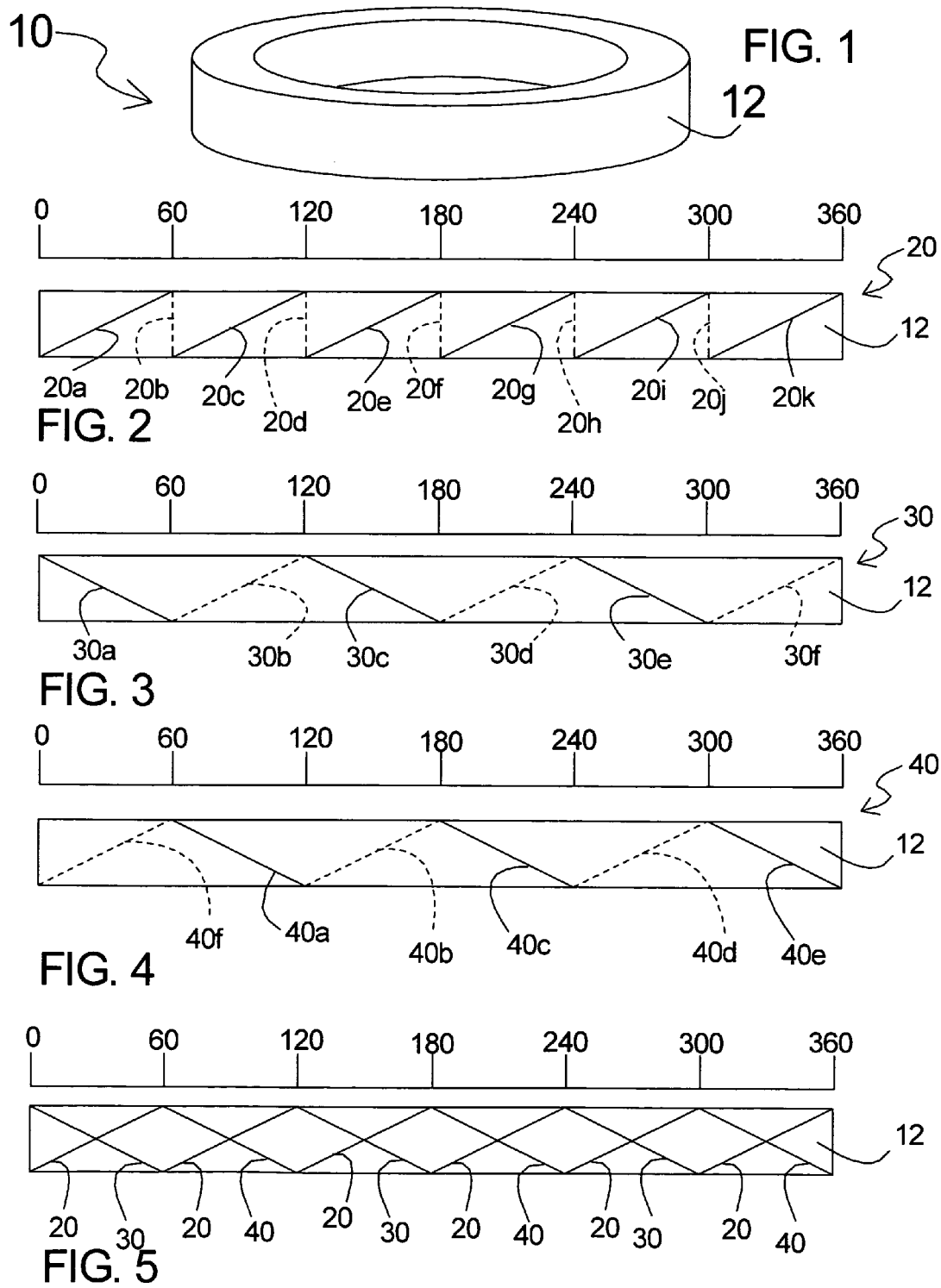

EDDY CURRENT PROBE

BACKGROUND OF THE INVENTION

Embodiments of the present invention relate generally to electronic sensing devices and particularly to eddy current probes.

Non-Destructive Examination (hereafter "NDE") of tubing in heat exchangers is essential to maintain the function of the unit, and to maintain the safety of plant workers and of the public. In particular, NDE of steam generators in nuclear plants is essential, as it allows for proactive repair of damaged tubes prior to costly unscheduled outages and/or significant safety-related events. Electromagnetic sensing devices, known as eddy current probes, are primarily used for such NDE. Generally, the probe resides at one end of a cable with the other end presenting an electrical connection to a remote data acquisition unit (RDAU) for collecting and analyzing the signal data. The probe is inserted into heat exchanger tubing and the signals produced thereby are transmitted along the cable and to the remote data acquisition unit. Signals taken from the probe provide indication of tube conditions including a variety of defects and anomalies of interest.

Eddy current probes for tubing can assume a number of different forms. Historically, there have been three general classifications of eddy current probes for heat exchanger and other tubing inspections: bobbin, array, and rotating.

Bobbin probes include a differential pair of annular (ring shaped) coils pulled through a given length of tubing. The coil turns are coaxial with the axis of the tubing. Bobbin probes provide the simplest exam and operate at relatively high speeds. Data acquisition speed is rapid with a simple single channel analysis. This type of probe is most common, as it is simple to build and is least expensive. Due to their simplicity, and due to their potential for testing at high speeds, bobbin probes are used for the majority of heat-transfer areas in a steam generator. There are, however, distinct limits to the size and location of flaws that may be detected with a bobbin probe. Bobbin probes are not adequate for detecting certain types of flaws, or for providing accurate depth and/or length information about a particular flaw. For example, the circumferential windings of a bobbin probe prevent reliable detection of circumferential defects, regardless of their location. For detection of circumferential flaws or smaller axial flaws in areas known to produce unwanted signal noise is required, bobbin probes do not provide acceptable performance. Consequently, certain areas of a steam generator require the use of the more sophisticated rotating or array probes.

Rotating probes involve the use of a motor, usually separate from the probe head, to mechanically spin a smaller, more focused coil within a length of tubing. The whole assembly is withdrawn from the tube at a slow rate of speed, e.g., 0.4 to 0.6 inches per second. As the probe spins it moves along a helical scan path within the tube. When properly used with a trigger pulse channel, rotating probe data may be presented in an isometric view, known as a "C-scan" for enhanced flaw detection and characterization. Although the merits of rotating probe inspection are widely known, the speed of data acquisition and analysis are relatively slow. Acquisition speed using rotating probes can be as much as 100 times slower than bobbin exams. The volume of data required is also much higher. For example, in a ⅞" diameter tubing a rotating probe travels 876 helical inches to inspect 12 inches of tubing and creates a data file 73 times larger than a bobbin probe data file.

Thus, while significantly slower than bobbin examinations, rotating probe examinations offer enhanced detection, detailed sizing, and better characterization. This is particularly true in the case of circumferential cracks, to which bobbin probes are insensitive. The insensitivity of bobbin probes to circumferential cracks can be attributed to the fact that the coils are wound in the same plane as the defect, resulting in little or no interruption of eddy currents in the tube; a condition required for detection. Bobbin probes are primarily sensitive to axial (longitudinal) cracks, and volumetric defects like pits, while rotating pancake or rotating orthogonal coil arrangements allow for detection and characterization of circumferential cracks.

The presence of circumferential cracks has long been thought to be limited to the "Top-of-Tube Sheet" (TTS) area of steam generators. Consequently, rotating probe examinations have been primarily used only in this small region. One exception includes dented tubes that must be inspected with rotating probes due to bobbin signal interference, or noise, caused by dents. Circumferential cracks have been found, however, in certain nuclear plants. This has created a requirement for all nuclear plants at risk to inspect all U-bends for circumferential cracks. U-bend inspection, however, encompasses a relatively large surface area as compared to the relatively smaller surface area inspected in a TTS inspection. For this reason, detecting circumferential cracks, especially at U-bends, calls for a method of detection faster than that of rotating probes.

Array probes provide a partial solution to the acquisition speed problems posed by rotating probes. By positioning a number of coils in an array around the circumference of a probe, array probes offer 360-degree coverage without the need to rotate a single coil. Array probes may therefore be withdrawn from the tube at a higher rate of speed than rotating probes (typically 10-12 inches per second).

Several different multi-coil array probes have been proposed and used. Generally, these probes offer a pull-through method of inspection with as many as 32 coils designed to duplicate RPC responses at much faster speeds. These array probes can provide adequate detection of circumferential cracks. However, array probes produce a high volume of data, e.g., 32 coil elements operating at 4 frequencies produce 128 data channels. As a result, data analysis becomes time-consuming. Further, array probes are highly sensitive and can reveal flaw indications falling below the interest level of the utility. Nevertheless, all flaw indications must be analyzed and suitably rectified in accordance with applicable regulations and guidelines. This exhaustive and often unproductive work is an unwelcome feature of the array probe inspection method.

A need thereby exists for an eddy current probe capable of detecting a full range of defect types at high inspection speeds without a corresponding high volume of data. Embodiments of the present invention provide such high-speed inspection with reasonable volumes of data.

SUMMARY OF THE INVENTION

An eddy current probe moves along a longitudinal axis and includes a support structure defining a surface, the surface including a set of panels. Conductor coils are distributed across said surface, each panel includes at least one coil section, each coil section lies transverse to the longitudinal axis.

BRIEF DESCRIPTION OF THE DRAWINGS

For a better understanding of embodiments of the invention, and to show how the same may be carried into effect, reference will now be made, by way of example, to the accompanying drawings in which:

FIG. 1 illustrates an annular core used a structure supporting eddy conductor coils thereon according to certain embodiments of the present invention.

FIGS. 2-10 illustrate a variety of conductor winding patterns used to form conductor coils on the core of FIG. 1.

DETAILED DESCRIPTION OF EMBODIMENTS

Figure 6:
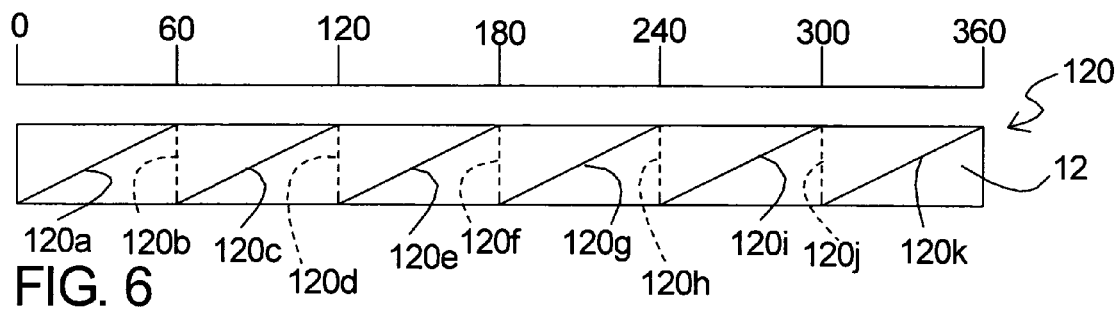

In accordance with embodiments described herein, a plurality of insulated copper wire windings act as an eddy current sensor for the detection and characterization of various anomalies within non-ferrous and ferrous tubing when used with certain impedance analyzing equipment. Generally, eddy current probes as described herein may be characterized as multi-axis transmit/receive inspection probes. Among the variety of embodiments of the present invention, embodiments described herein include 3-coil (single transmit with differential pickup), 2-coil (single transmit with single receive coil), 2-coil differential, 2-coil external reference differential, and 3-coil remote field (RFT).

FIG. 1 illustrates an annular probe core 10. Core 10 is typically non-ferrous, but could in certain applications be ferrous. Embodiments of the present invention illustrated herein make use of a non-ferrous core 10. Core 10 presents a generally rectangular cross-section and includes an outward facing cylindrical surface 12. It will be understood, however, that the present invention is not limited to a particular cross-sectional shape for core 10. For purposes of illustration, FIGS. 2-5 show surface 12 as if rolled out into a planar form. In this manner, the entire surface 12 can be illustrated in one figure. It will be understood, however, that in the particular embodiments shown surface 12 is a cylindrical surface. The present invention is not limited to a cylindrical surface 12. As a reference, FIGS. 2-5 indicate 0 degrees at the left and 360 degrees at the right. Thus, in the right and left edges of surface 12 as shown in FIGS. 2-5 are actually contiguous.

Coil conductors as provided according to embodiments of the present invention are distributed across surface 12 by wrapping conductors along generally helical paths about core 12. A selected number of coil sections or panels can be established upon surface 12. Each section or panel occupies a corresponding portion of surface 12. Thus, if six coil sections are selected, each section occupies 60 degrees (360/6) of surface 12. For two coil sections, each occupies 180 degrees. The following examples describe probes having six coil sections, but it will be understood that the present invention is not limited to a particular number of coil sections pr surface 12 panels.

FIG. 2 illustrates a winding pattern 20. In FIG. 2, winding pattern 20 begins at 0 degrees and at the bottom edge of surface 12. Path 20 extends angularly toward the top edge of surface 12 a given number of degrees. In the present example, surface 12 presents six coil sections, each section occupying 60 degrees. Accordingly, the first leg 20a of pattern 20 extends from 0 degrees through 60 degrees as it traverses surface 12 from the bottom edge to the top edge. The second leg 20b of pattern 20 passes over the top, through the interior, and under the bottom of core 10 and ends at the bottom edge of surface 12 at 60 degrees. The third leg 20c of pattern 20 extends from the bottom edge of surface 12 toward the top edge of surface 12 from 60 degrees through 120 degrees. This pattern continues whereby surface 12 carries legs 20a, 20c, 20e, 20g, 20i, and 20k in the first, second, third, fourth, fifth, and sixth panels or sections, respectively, of surface 12.

FIG. 3 illustrates a winding pattern 30. In FIG. 3, a first leg 30a of pattern 30 begins at the top edge of surface 12 and extends toward the bottom edge of surface 12 from 0 degrees through 60 degrees. A second leg 30b of pattern 30 goes under core 10, through the interior of core 10, and over the top of core 10 and reaches the top edge of surface 12 at 120 degrees. The third leg 30c then traverses surface 12 extending from the top edge of surface 12 toward the bottom edge of surface 12 and extending from 120 degrees through 180 degrees. A fourth leg 30d then wraps under, behind, and over core 10 to reach surface 12 at its top edge at 240 degrees. Leg 30e crosses surface 12 from the top edge to the bottom edge and from 240 degrees through 300 degrees. The final leg 30f wraps under, behind, and over core 10 to reach surface 12 at its top edge at 0 or 360 degrees.

Thus, pattern 30 presents on surface 12 legs 30a, 30c, 30e in alternating panels or sections of surface 12, e.g., from 0 degrees through 60 degrees, from 120 degrees through 180 degrees, and from 240 degrees through 300 degrees.

FIG. 4 illustrates a winding pattern 40. In FIG. 4, a first leg 40a of pattern 40 begins at the top edge of surface 12 and extends toward the bottom edge of surface 12 from 60 degrees through 120 degrees. A second leg 40b of pattern 40 goes under core 10, through the interior of core 10, and over the top of core 10 and reaches the top edge of surface 12 at 180 degrees. The third leg 40c then traverses surface 12 extending from the top edge of surface 12 toward the bottom edge of surface 12 and from 180 degrees through 240 degrees. A fourth leg 40d then wraps under, behind, and over core 10 to reach surface 12 at its top edge at 300 degrees. Leg 30e crosses surface 12 from the top edge to the bottom edge and from 300 degrees through 360 degrees. The final leg 30f wraps under, behind, and over core 10 to reach surface 12 at its top edge at 60 degrees.

Thus, pattern 40 is similar to pattern 30 but is radially offset whereby legs 40a, 40c, 40e occupy alternating panels or sections of surface 12 not taken by pattern 30, e.g., from 60 degrees through 120 degrees, from 180 degrees through 240 degrees, and from 300 degrees through 360 degrees. In other words, patterns 30 and 40 interleave relative to surface 12 each presenting a coil section in alternating panels of surface 12. For a probe with six coil sections, pattern 30 occupies the first, third, and fifth panels or sections of surface 12 while pattern 40 occupies the second, fourth, and sixth panels or sections of surface 12. For a probe with eight coil sections, pattern 30 occupies the first, third, fifth, and seventh panels or sections of surface 12 while pattern 40 occupies the second, fourth, sixth, and eighth panels or sections of surface 12.

Core 10 can include a recess or groove along patterns 20, 30, and 40 whereby insulated conductors can be wrapped within the recesses and helically about core 10 along patterns 20, 30, and 40.

FIG. 5 illustrates surface 12 with patterns 20, 30, and 40 thereon. In each of the panels of surface 12, pattern 20 crosses either pattern 30 or pattern 40. The relative angle of intersection between pattern 20 and either pattern 30 or 40 relative to pattern 20 can vary, but a 90-degree angular relationship has proven effective. It will be understood, however, that the present invention is not limited to a particular angular relationship at the intersection of pattern 20 and either pattern 30 or pattern 40.

To construct a probe having three coils, one winds a conductor along each of patterns 20, 30 and 40. As noted, grooves (not shown) cut into core 10 and along patterns 20, 30, and 40 guide and fix placement of the coil conductors. For example, a relatively deeper groove along pattern 20 receives a first conductor by iteratively winding the conductor along pattern 20. In other words, each turn of the conductor encompasses the entire pattern 20. the number of passes around pattern 20 determines the number of windings or turn for that coil. By making the groove for pattern 20 deepest, the coil placed therein lies behind the coils placed along patterns 30 and 40. Thus, grooves cut for patterns 30 and 40 can be the same depth, but more shallow than a groove cut for pattern 20. A second conductor is wrapped iteratively along pattern 30 a selected number of turn to establish a second coil. A third conductor is wrapped iteratively along pattern 40 to form a third coil.

Thus, a three coil probe results. Each conductor has a start terminal and a finish terminal, thereby presenting six terminals overall. A variety of wiring arrangements are then possible to these conductor terminals. In use, core 10 with conductor coils wrapped thereon moves co-axially along a tube while signals are taken from or applied to the coils. Thus, according to one form of probe, multiple coils posses multiple axes relative to the tube axis and can serve a variety of transmit and receive functions according to a particular inspection method chosen.

FIG. 6 illustrates a winding pattern 120 similar to pattern 20 in that it distributes a coil conductor across consecutive panels of surface 12. Pattern 120 differs, however, in that it produces a set of coil segments, one coil segment in each panel of surface 12, coupled in series around core 10. Pattern 120 begins at the bottom edge of surface 12 and extends along a leg 120a toward the top edge of surface 12 and across the first panel of surface 12, e.g. from 0 degrees through 60 degrees. A corresponding return leg (not shown) passes over, behind, and under core 10 to reappear at the bottom of surface 12 and the beginning of the first panel. Iteratively winding a conductor along leg 120 and its corresponding return leg forms a coil segment of a selected number of turns in the first panel of surface 12. A series connection leg 120b takes the conductor from the first panel to the second panel and appears at the bottom edge of surface 12 and the beginning of the second panel, e.g. at 60 degrees in the particular embodiment illustrated. Pattern 120 continues with a leg 120c traversing the second panel from the bottom edge to the top edge. A corresponding return leg (not shown) passes over, behind, and under core 10 to reappear at the bottom of surface 12 and the beginning of the second panel. Iteratively winding a conductor along leg 120b and its corresponding return leg forms a coil segment in the second panel of surface 12. A series connection leg 120d takes the conductor from the second panel to the third panel and appears at the bottom edge of surface 12 and at the beginning of the third panel, e.g. at 120 degrees in the particular embodiment illustrated.

Pattern 120 continues whereby each of legs 120e, 120g, 120i, and 120k have a corresponding return leg (not shown) and a coil segment forms in each panel of surface 12 by iteratively wrapping the conductor along one of legs 120e, 120g, 120i, and 120k and its corresponding return leg. Thus, coil segments form in each of the third, fourth, fifth, and sixth panels of surface 12. Series connection legs 120d, 120f, 120h, and 120j couple in series the coil segments in each of the surface 12 panels. Overall, a coil segment appears in each panel of surface 12 with the set of coil segments coupled in series.

Figure 7:
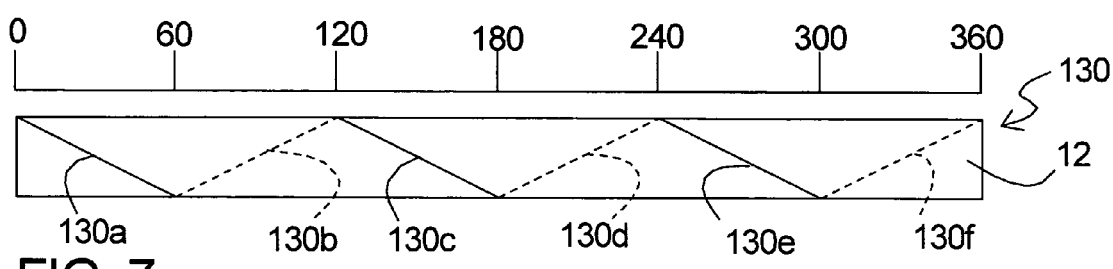

FIG. 7 illustrates a winding pattern 130 similar to pattern 30 in that it distributes a coil conductor across alternating panels of surface 12. Pattern 130 differs, however, in that it produces a set of coil segments, one coil segment in each alternating panel of surface 12, coupled in series around core 10. Pattern 130 begins at the top edge of surface 12 and extends along a leg 130a toward the bottom edge of surface 12 and across the first panel of surface 12, e.g. from 0 degrees through 60 degrees. A corresponding return leg (not shown) passes under, behind, and over core 10 to reappear at the top of surface 12 and the beginning of the first panel. Iteratively winding a conductor along leg 130a and its corresponding return leg forms a coil segment of a selected number of turns in the first panel of surface 12. A series connection leg 130b takes the conductor from the first panel to the third panel and appears at the top edge of surface 12 and the beginning of the third panel, e.g. at 120 degrees in the particular embodiment illustrated. Pattern 130 continues with a leg 130c traversing the third panel from the top edge to the bottom edge. A corresponding return leg (not shown) passes under, behind, and over core 10 to reappear at the top of surface 12 and the beginning of the third panel. Iteratively winding a conductor along leg 130c and its corresponding return leg forms a coil segment in the third panel of surface 12. A series connection leg 120d takes the conductor from the third panel to the fifth panel and appears at the top edge of surface 12 and at the beginning of the fifth panel, e.g. at 240 degrees in the particular embodiment illustrated. Iteratively winding a conductor along leg 130e and its corresponding return leg forms a coil segment in the fifth panel of surface 12. A series connection leg 130f takes the conductor from the fifth panel to the first panel and appears at the bottom edge of surface 12 and at the beginning of the first panel, e.g. at 360 or 0 degrees in the particular embodiment illustrated.

Thus, coil segments form in alternating panels of surface 12 with a series connection therealong and about core 10.

Figure 8:
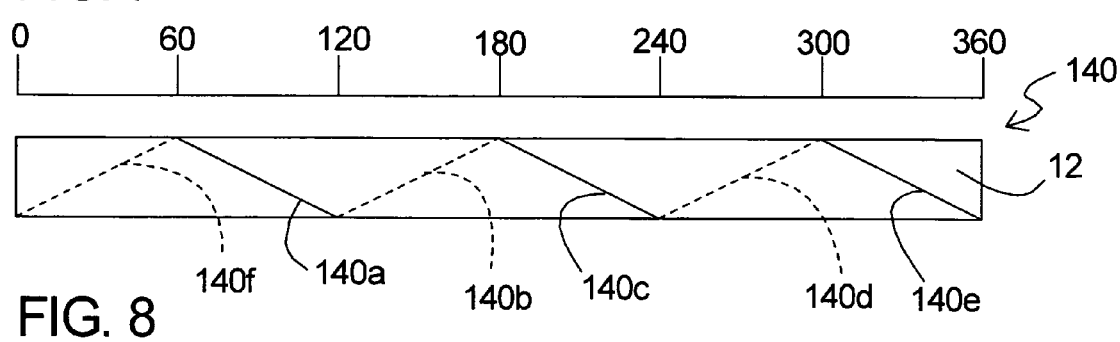

FIG. 8 illustrates a winding pattern 140 similar to pattern 130, but radially offset to occupy panels of surface 12 not taken by pattern 130. Thus, each of legs 140a, 140c, and 140e has a corresponding return leg (not shown). A first coil segment forms in the second panel of surface 12 by iteratively winding the conductor along leg 140a and its corresponding return leg over, behind and under core 10. A series connection leg 140b couples the coil segment of the second panel with a coil segment in the fourth panel formed by iteratively winding along leg 140c and its corresponding return leg. A series connection leg 140d couples the coil segment of the fourth panel with a coil segment in the sixth panel formed by iteratively winding along leg 140e and its corresponding return leg. A series connection leg 140f couple the coil segment of the sixth panel with the coil segment of the second panel.

A combination of patterns 120, 130, and 140 appear similar to that of patterns 20, 30, and 40 as portrayed in FIG. 5. In other words, as seen from the exterior of core 10, the coil windings have a similar appearance across surface 12 as that of patterns 20, 30, and 40. The difference being that patterns 120, 130, and 140 form multiple series-connected coil segments in selected panels of surface 12.

Figure 9:
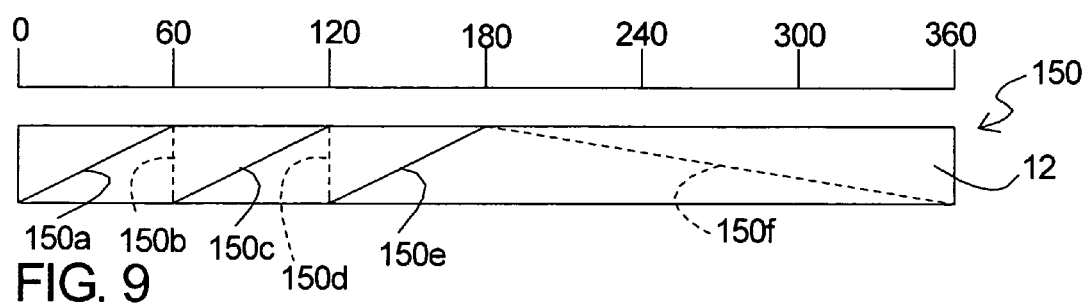
Figure 10:
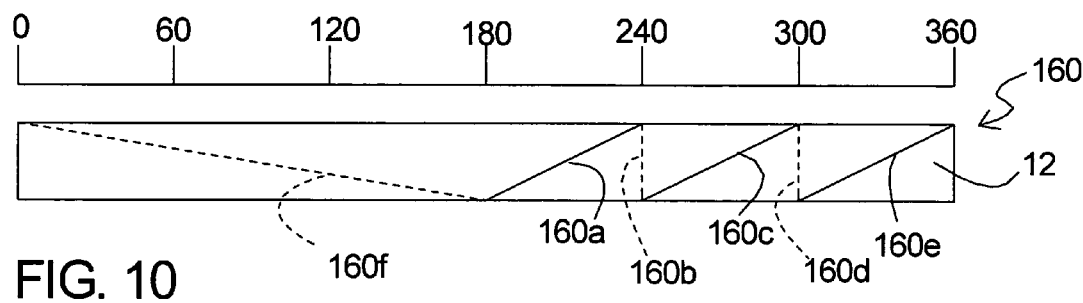

FIGS. 9 and 10 illustrate winding patterns 150 and 160, respectively. Winding patterns 150 and 160 are similar to winding patterns 20 and 120 in that consecutive panels of surface 12 bear coil conductors. However, under patterns 150 and 160, not all panels of surface 12 bear coil conductors. For example, pattern 150 distributes coil conductors across the first half of panels of surface 12 and pattern 160 distribute coil conductor across the second half of panels. Thus, for a 6-panel arrangement, pattern 150 places coil conductors on the first, second, and third panels of surface 12 and pattern 160 places coil conductors across the fourth, fifth and sixth panels of surface 12. Patterns 150 and 160 place the coil conductors at the same angle relative to the tube axis and cooperate to fill all panels with two coils. Pattern 150 can be implemented in a manner similar to pattern 20 whereby each turn or winding traverses consecutively legs 150a, 150b, 150c, 150d, 150e and 150f. Iteratively following these legs creates a coil presentation in the first three panels of surface 12. Similarly, pattern 160 may be followed iteratively along consecutive legs 160a, 160b, 160c, 160d, 150e, and 160f to form a coil presentation in the last three panels of surface 12.

In the alternative, an arrangement similar to patterns 120 may be implemented whereby winding occurs iteratively along leg 150a and a return leg (not shown) over, behind, and under core 10 to produce a coil segment in the first panel of surface 12. In such case, leg 150b of FIG. 9 represents a series connection leg to the second panel whereat wrapping iterate along leg 150c and a corresponding return leg (not shown) over, behind, and under core 10 to produce a coil segment in the second panel. The pattern continues with a third coil segment formed in the third panel by iterative wrapping along leg 150e and a corresponding return leg (not shown) with leg 150d representing a series connection leg from the second panel to the third panel. A similar method of implementation may be applied to pattern 160, resulting in separate coil segments each along legs 160a, 160c, and 160e, respectively, and their corresponding return legs (not shown) with legs 160b and 160d providing series connection legs therealong.

As illustrated herein, surface 12 is represented in planar form for simplified illustration, but a probe according to embodiments of the present invention can be implemented in planar form, much as illustrated herein, and applied to planar or generally planar surfaces. For example, such a planar form of probe can be used to inspect around rivets or fasteners along a planar or substantially planar surface, e.g. as in aircraft applications. Accordingly, the particular contour of surface 12 may be selected according to a particular application, e.g., cylindrical in the case of tube inspection or generally planar in the case of fastener inspection. It will be understood, therefore, that the present invention is not limited to a particular geometric shape for surface 12.

Probes according to embodiments of the present invention, though possessing a number of similarities to bobbin and array probes, are actually quite different. Probes according to embodiments of the present invention can include a three-coil probe, consisting of a single transmit coil, and two receiver coils. As described above, each of the three coils may actually consist of a number (undefined) of shorter coil segments connected in series. These coils may be tipped at an angle (typically between 0 and 90 degrees) to the tube axis. The angle is chosen based on the desired detection of the probe. Coils tipped more dramatically from the tube axis will have a greater propensity to detect axial flaws with the tube. Flaws oriented more closely to the tube axis (including 0 degree axial coils) will have a propensity to detect circumferentially oriented flaws. By orienting probes according to embodiments of the present invention at 45 degrees to the tube axis, the probe is able to detect axial and circumferential flaws equally. Probes according to embodiments of the present invention are pulled through the tube at a high rate of speed, with no rotation required.

Another feature of the probes according to embodiments of the present invention is common-mode cancellation of many annular sources of noise within heat exchanger tubing. These annular sources of noise include radial dents, tube support plate intersections, and tube expansions, which can often mask flaw signals when using other eddy current techniques. Because in probes according to embodiments of the present invention the receiver coils occupy the same axial space within a probe, they sense these approaching annular anomalies at the same time, thus canceling out the response. Tiny flaws located in these areas are thereby more readily detected.

Probes according to embodiments of the present invention also have cross-sectional linear symmetry, and can thus be relied upon to suppress two-sided sources of noise within heat exchanger tubing. These noise sources include the oval cross-section of U-bends, two-sided egg-crate supports, and two-sided dents (common in steam generators containing egg-crate tube supports).

Although probes according to embodiments of the present invention may possess as many as three coils, the user may choose to actually employ a lower number by modifying the configuration of the tester (RDAU). For example, a three-coil probe may be operated in impedance differential mode, in which case the transmit coil is not used. In transmit/receive mode, the transmit coil creates a magnetic field inducing eddy currents in the tube; while the two receive coils passively monitor impedance changes. In either of the above cases, the result is only one channel of data. Therefore, high acquisition speeds can be used, and low volume of data is produced. The efficiency of acquisition and analysis is thereby improved over rotating and array probe exams.

To compare with the smaller, more focused coils found in rotating and array probes in the realm of detection capability, probe coils according to embodiments of the present invention can be driven with relatively higher voltages and gain settings than other probes. In addition, transmit/receive windings have been designed according to embodiments of the present invention to act as a step-up transformer to further increase signal amplitude. This is achieved by the presence of a higher number of turns on the receive coil winding than on the transmit coil winding. The result is detection ability comparable to rotating probes and array probes, even though the probes according to embodiments of the present invention cover 25 times the area of typical rotating probe coils.

In a 3-coil single transmit with differential pickup embodiment, a single transmit coil is wound helically, e.g., according to pattern 20 or pattern 120, into grooves around an air-core torus. The grooves may be oriented at plus or minus 45 degrees to the tube axis, plus or minus 22.5 degrees to the tube axis, or at any other angle to the tube axis between 0 and 90 degrees. The number of grooves in each direction may vary from as few as two to as many as twelve or more. A pair of receive coils is then wound helically into alternating grooves, e.g., according to pattern 30 or 130 for one coil and according to pattern 40 or 140 for the other coil, oriented opposite to the transmit coil grooves, intersecting at their centers. Each receive coil uses half as many grooves as the transmit coil. In a 12-groove or 12 panel example, while the transmit coil occupies all twelve grooves or panels according to pattern 20 or 120 with a particular orientation, each receive coil only occupies six grooves or panels with an opposite orientation, in an alternating fashion.

Within this embodiment are several different methods of manufacturing. In one case, the transmit coil is wound completely into deeper grooves, followed by the two receive coils being wound into shallower grooves. The driver coil thereby actually fits inside the receiver coils, forming concentric helixes. In another version, the two receive coils are wound first into deeper grooves, followed by the transmit coil being wound into shallower grooves, also forming concentric helixes. Finally, the transmit coil and both receive coils may also be wound layer by layer in an interleaved fashion into equal depth grooves. The performance of this version is the highest; due to transmit and receive coils being nearly equidistant from the tube inner wall, whereas each of the previously described versions have either the transmit coil or the receive coil positioned closer to the tube wall than the other. Notwithstanding, the difficulty in manufacturing the interleaved version is also the highest.

The advantages of a coil assembly wound according to the embodiments of the present invention are manifold. Since the two receive coils occupy the same longitudinal space within the probe, and because they are differentially opposed to each other (either by reverse polarity or by a subtractive algorithm within the impedance analyzing equipment), there is a near total cancellation (suppression) of many sources of interference to the process of flaw detection (noise). Among the sources of noise suppressed by the probe are tube expansions (i.e. TTS or Top of Tube Sheet), Tube Support Plates (TSPs), U-bend geometry (oval cross-section), and dents. Since flaws commonly occur at these locations, the suppression of noise offered by probes according to embodiments of the present invention are desirable. Also, the available off-axis orientation of both transmit and receive coils in a probe according to embodiments of the present invention allows for detection of both axial and circumferential defects (cracks) within tubing. Conventional, high-speed screening probes like annular bobbin probes do not offer the detection of circumferential defects, as the coil windings must be other than parallel to the flaw of interest to provide such detection. Since the windings of a conventional bobbin probe are circumferential, they are insensitive to circumferential defects In a 2-coil single transmit with single receive coil embodiment, a single transmit coil is wound into a number of grooves oriented in a particular direction from the tube axis. A single receive coil is then wound into an equal number of grooves oriented in an opposite direction from the tube axis. As with the 3-coil version described above, this version may be manufactured with concentric helixes using different groove depths, or it may be manufactured in an interleaved fashion, with alternating layers assigned to each coil in equal depth grooves.

In a 2-coil differential embodiment, two coils are wound in alternating grooves or panels in a single direction. In other words, construction is exactly like the differential pair of receive coils described in the 3-coil version above but without use of transmit coil. Or, the coils may be wound in an interleaved fashion into equal depth grooves in opposite directions to each other. In either case, the coils match each other in number of turns, DC resistance, and inductance to allow for proper balance of the Wheatstone bridge. As previously stated, the presence of a third coil (transmit coil) does not prohibit the use of two-coil differential embodiment, in which case, the transmit coil is simply not used.

In some cases, proper flaw detection and characterization is not possible with either conventional differential probes, or with differential transmit/receive probes, regardless of their construction. An example is any anomaly occurring gradually over an extended length of tubing (like tube-to-tube thinning). The comparison of two coils in close proximity to each other is not sufficient to allow detection of gradual thinning occurring over several inches of tubing.

With a 2-coil external reference differential embodiment, however, an external reference differential allows for such detection. A single receive coil from one probe inside a test specimen is compared in differential mode to an equivalent coil from a second reference probe placed inside controlled, unflawed tubing (a reference standard). The result is a strong absolute signal from gradual flaws occurring over some distance. Furthermore, these external reference channels provide a means for locating probe position relative to various structures within a heat exchanger (such as tube support plates and tube expansions, which are otherwise suppressed on differential channels). The external reference method of testing is usually possible without any physical modifications to probe construction, but is managed through the test instrument and its controlling software. Probes according to embodiments of the present invention, are compatible with this sort of testing. Use of such external reference differential testing is a preferred supplement to either transmit/receive differential or impedance differential testing. Some RDAUs allow for monitoring both receiver coils in external reference mode. This represents the ideal situation, as the external reference channels can then be reliably used to supplement detection for the entire 360 degree tube circumference.

In a 3-coil remote field (RFT) embodiment, a large annular driver coil is placed several inches (typically 2-3 tube diameters) away from a helical pair of alternating receive coils (as described above). The advantage of this embodiment is utilizing the remote field eddy current zone to allow for inspection of ferrous tubes (carbon steel, monel, nickel, 400 series stainless steel, etc.). The concept of using remote field is widely accepted for testing ferrous tubes, but adding the helical pair of differential receive coils may add some advantages, including the elimination of TSP or baffle plate signals from differential RFT responses.

Figure 11:
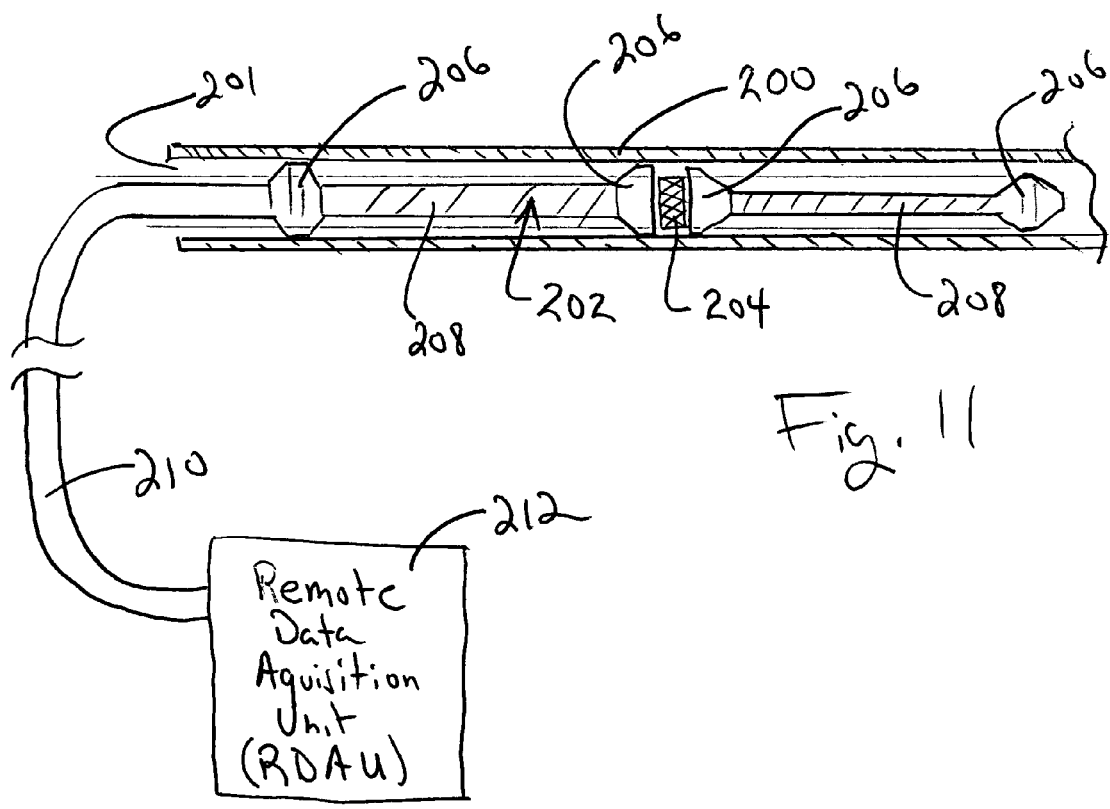
FIG. 11 illustrates an eddy current probe making use of sensor coils as formed according to the winding patterns of FIGS. 2-10

FIG. 11 illustrates a typical application of embodiments of the present invention as used to inspect a tube 200. Probe 202 inserts into an opening 201 of tube 200. Probe 202 includes a eddy current sensor 204 assembled according to a variety of methods as described herein, e.g., including coils form along patterns 20, 30, 40, 120, 130, 140, 150, or 160. Probe 202 also includes guide blocks 206 and flexible couplings 208 therebetween. Cable 210 extends from probe 202 to an RDAU 212 located externally of tube 200. A variety of configurations may be implemented using RDAU 212 to make use of signals applied to and taken from probe 202. As probe 202 moves within tube 200, signal taken from probe 202 provide indication of the condition of tube 200, e.g., identification of defects, flaws and anomalies of interest. RDAU collects and analyses signal data to report such indications of interest.

It will be appreciated that the present invention is not restricted to the particular embodiments that have been described and illustrated, and that variations may be made therein without departing from the scope of the invention as found in the appended claims and equivalents thereof.

What is claimed is:

1. An eddy current probe for analyzing tubular specimens, the eddy current probe comprising:
    an annular core defining an outer surface and an axis;
    a first coil conductor wound about the annular core to define a first plurality of winding sections spaced about the annular core and disposed at an acute angle relative to the axis, the first coil conductor being configured for detecting changes in the flow of eddy currents in a tubular specimen; and
    a second coil conductor wound about the annular core to define a second plurality of winding sections spaced about the annular core and disposed at an acute angle relative to the axis of between 22.5 degrees and 67.5 degrees, the second coil conductor is configured for detecting changes in the flow of eddy currents in the tubular specimen;
    wherein the first plurality of winding sections are disposed at the same axial position as the second plurality of winding sections.

2. The eddy current probe of claim 1, wherein the first plurality of winding sections and the second plurality of winding sections are disposed at the same acute angle.

3. The eddy current probe of claim 2, wherein the acute angle is about 45 degrees.

4. The eddy current probe of claim 1, wherein the first and second coil conductors are interconnected in a differential bridge circuit to provide a differential pickup.

5. The eddy current probe of claim 1, further comprising a third coil conductor wound about the annular core to define a third plurality of winding sections spaced about the annular core and disposed at an acute angle relative to the axis, the third coil conductor being disposed at the same axial position as the first and second coil conductors.

6. The eddy current probe of claim 5, wherein the third coil conductor comprises a transmit coil, and the first and second coil conductors comprise differential pickup receiver coils.

7. The eddy current probe of claim 6, wherein the first and second coil conductors match each other in number of turns, resistance and inductance to allow for proper balance of a differential bridge circuit.

8. The eddy current probe of claim 1, wherein the first plurality of winding sections are each individually sequentially wound before proceeding to the next winding section.

9. The eddy current probe of claim 1, wherein the annular core defines a plurality of channels on the outer surface, and wherein the first plurality of winding sections are disposed in the plurality of channels.

10. The eddy current probe of claim 1, further comprising a third conductor coil comprising a large driver coil that is disposed distally away from the first and second conductor coils.

* * * * *